(12) United States Patent
Shi

(10) Patent No.: US 9,636,141 B2
(45) Date of Patent: May 2, 2017

(54) DISPOSABLE SCALPEL BLADE ASSEMBLY AND SUPPORTING REUSABLE SCALPEL HANDLE

(71) Applicant: STERILANCE MEDICAL (SUZHOU) INC., Suzhou, Jiangsu (CN)

(72) Inventor: Guoping Shi, Jiangsu (CN)

(73) Assignee: STERILANCE MEDICAL (SUZHOU) INC., Suzhou (CN)

( * ) Notice: Subject to any disclaimer, the term of this patent is extended or adjusted under 35 U.S.C. 154(b) by 320 days.

(21) Appl. No.: 14/424,739

(22) PCT Filed: Sep. 2, 2013

(86) PCT No.: PCT/CN2013/082815
§ 371 (c)(1),
(2) Date: Feb. 27, 2015

(87) PCT Pub. No.: WO2014/036920
PCT Pub. Date: Mar. 13, 2014

(65) Prior Publication Data
US 2015/0201957 A1     Jul. 23, 2015

(30) Foreign Application Priority Data

Sep. 5, 2012   (CN) .......................... 2012 1 0324475

(51) Int. Cl.
*A61B 17/3211* (2006.01)
*A61B 17/3213* (2006.01)
(Continued)

(52) U.S. Cl.
CPC ...... *A61B 17/3213* (2013.01); *A61B 17/3217* (2013.01); *A61B 2017/32113* (2013.01); *A61B 2090/0814* (2016.02)

(58) Field of Classification Search
CPC ...... A61B 17/3211; A61B 2017/32113; A61B 2017/32116; B26B 1/10; B26B 5/002; B26B 5/003; B26B 5/005–5/008
(Continued)

(56) References Cited

U.S. PATENT DOCUMENTS

| 4,232,445 A * | 11/1980 | Ito | ........................... B26B 5/002 |
| | | | 30/162 |
| 4,322,885 A * | 4/1982 | Osada | ..................... B26B 5/002 |
| | | | 30/162 |

(Continued)

FOREIGN PATENT DOCUMENTS

| CN | 102835992 A | 12/2012 |
| CN | 102871706 A | 1/2013 |

OTHER PUBLICATIONS

Dec. 13, 2013 International Search Report issued in PCT/CN2013/082815.
Dec. 12, 2013 Written Opinion issued in PCT/2013/082815.

*Primary Examiner* — Richard Crosby, Jr.
(74) *Attorney, Agent, or Firm* — Oliff PLC

(57) ABSTRACT

Disposable scalpel blade assembly and supporting reusable handle. The blade assembly includes a blade, blade holder and blade shield. The blade holder has a flexible arm at the rear-end, which has a protrusion-block at the arm end. The blade shield inner wall has clearance opening for the protrusion-block. When the handle is inserted, the protrusion-block extends into the clearance opening with sideward movement, so the blade and blade holder are connected. After the handle is pulled-out, the protrusion-block misaligns with the clearance opening and cannot make sideward movement so the handle cannot connect again. The blade holder first sliding channel is provided with a first front locking channel at its front-end and a deadlock channel is set in front of the first front locking channel. When the handle (Continued)

is pulled-out after use, the first protrusion of the blade shield shall fall into the deadlock channel to enter the deadlocking state.

9 Claims, 6 Drawing Sheets

(51) Int. Cl.
  *A61B 17/3217* (2006.01)
  *A61B 90/00* (2016.01)
(58) Field of Classification Search
  USPC ...... 30/151, 162; 15/145; 606/166, 167, 172
  See application file for complete search history.

(56) References Cited

U.S. PATENT DOCUMENTS

| | | | | |
|---|---|---|---|---|
| 5,299,357 | A * | 4/1994 | Wonderley | A61B 17/3211 30/320 |
| 5,417,704 | A * | 5/1995 | Wonderley | A61B 17/3211 30/162 |
| 5,497,553 | A * | 3/1996 | Chong | B26B 5/002 30/162 |
| 5,545,175 | A * | 8/1996 | Abidin | A61B 17/3211 30/162 |
| 5,741,289 | A * | 4/1998 | Jolly | A61B 17/3213 606/172 |
| D470,938 | S * | 2/2003 | Howell | A61B 17/3211 D24/147 |
| 6,626,925 | B2 * | 9/2003 | Newman | A61B 17/3213 30/151 |
| 6,629,985 | B1 * | 10/2003 | Kiehne | A61B 17/3213 30/162 |
| 7,314,471 | B2 * | 1/2008 | Holman | A61B 17/3213 606/167 |
| 7,346,989 | B2 * | 3/2008 | Shi | A61B 17/3213 30/151 |
| 7,909,840 | B2 * | 3/2011 | Cote | A61B 17/3211 606/167 |
| 8,015,712 | B2 * | 9/2011 | Yi | A61B 17/3213 30/162 |
| 8,114,103 | B2 * | 2/2012 | Rasco | A61B 17/3213 30/151 |
| 8,181,352 | B1 * | 5/2012 | Shackelford, Sr. | A61B 17/3213 30/162 |
| 2006/0212058 | A1 * | 9/2006 | Djordjevic | A61B 17/3213 606/167 |
| 2007/0255298 | A1 * | 11/2007 | Djordjevic | A61B 17/3213 606/167 |
| 2008/0086158 | A1 * | 4/2008 | Holman | A61B 17/3211 606/167 |
| 2015/0133986 | A1 * | 5/2015 | Vodinh | A61B 17/3211 606/172 |

* cited by examiner

DISPOSABLE SCALPEL BLADE ASSEMBLY AND SUPPORTING REUSABLE SCALPEL HANDLE

TECHNICAL FIELD

The present invention relates to a medical surgical scalpel, particularly to a kind of disposable scalpel blade assembly and supporting reusable scalpel handle.

BACKGROUND OF INVENTION

The scalpel is a necessary tool for surgical operation and its safety is extremely important to healthcare workers and patients. At present, a conventional scalpel consists of a metal handle and a disposable blade which is installed on the handle before use and removed from the handle after use. The installation and removal of a blade is a difficult and dangerous process, as the user is subject to the potential injury caused by an exposed or contaminated blade. Operating staff are prone to be hurt by the sharp instrument when passing the exposed scalpel to a colleague.

In order to improve the safety, existing surgical scalpels have been designed to incorporate the concept of carrying a shield. European patent EP0988832A2 discloses an invention patent application titled Surgical Scalpel applied by American BD Company (Becton, Dickinson Company). The surgical scalpel according to the patent application consists of a disposable blade assembly and a reusable handle. The blade assembly consists of a blade, blade holder and shield. Although this kind of sliding sleeve type surgical scalpel, by applying the shield structure, solves the safety problem caused by the exposed blade, it has not thoroughly solved the safety problem of reusing the scalpel. In other words, it's still possible to open and close the shield multiple times during use of the scalpel, so this kind of scalpel could not absolutely eliminate the possibility of reusing the scalpel.

Therefore, it's urgently necessary to invent a kind of safe and reliable scalpel, which could overcome the above described disadvantages of scalpels in prior art and serve the medical care industry better.

DISCLOSURE OF THE INVENTION

In view of the above described disadvantages of scalpels in prior art, the present invention is devised to provide a kind of disposable scalpel blade assembly and supporting reusable scalpel handle to solve the safety problem of reusing scalpels in prior art.

In order to achieve the above object, the present invention provides the technical solution of a disposable surgical blade assembly: a kind of disposable surgical blade assembly, which consists of a blade, blade holder and blade shield. The blade is fixed in the front portion of the blade holder and the blade shield is slidably mounted on the blade holder, wherein:

The said blade holder is provided with a flexible arm at the rear end which extends backwards and is used to connect the handle. The flexible arm is provided with a locking block used for engagement with a second inclined block at the front end of handle and a protrusion block used to prevent the deformation of the flexible arm. The protrusion block extends towards the inner wall of the blade shield and the inner wall of the blade shield is provided with a clearance opening for said protrusion block. Under the initial locating status of said blade assembly, the protrusion block faces the clearance opening. When the handle is inserted into the blade assembly to be connected with the blade holder, the second inclined block acts on the locking block to force the flexible arm to be flexed and force the protrusion block to extend into the clearance opening with a sideward movement. After the second inclined block travels across the locking block, the flexible arm automatically returns to its initial position resiliently and the second inclined block engages the locking block to connect the handle and blade holder; during removal of the handle, the second inclined block draws the blade holder backward with respect to the blade shield through the locking block to force the protrusion block to misalign with the clearance opening. In this condition, the handle cannot be re-inserted into the blade assembly and connected with blade holder as the protrusion block cannot make sideward movement through the clearance opening.

The above described technical solution is explained as follows:

1. In the above described technical solution, in order to further improve the safety of the scalpel, the said blade shield is provided with one top unlocking button, which is the first flexible cantilever structure on the blade shield. The first flexible cantilever is provided with a second locking protrusion, which includes a first protrusion; the blade holder is provided with a first sliding channel which corresponds with the first protrusion, and the first sliding channel is arranged along the blade holder with respect to the sliding direction of the blade shield. The first sliding channel is provided with the first front locking channel at its front end and the first front locking channel is connected with the front end of the first sliding channel. The deadlock channel is set in front of the first front locking channel and the locking block is set between the deadlock channel and the first front locking channel; during the operation process of the scalpel, the first protrusion forms the following different states when it mates with the first front locking channel, first sliding channel and deadlock channel respectively:

a. When the first protrusion is located in the first front locking channel, the blade is arranged inside the blade shield and the blade holder and blade are in a locking state with respect to the blade shield;

b. When the top unlocking button is pressed, the top unlocking button forces the first protrusion to move from the first front locking channel to the first sliding channel and under such state, the blade shield is allowed to move with respect to the blade holder and blade;

c. When the first protrusion travels from the first front locking channel across the locking block to fall in the deadlock channel, the blade is arranged inside the blade shield and the blade holder and blade are in a deadlocking state with respect to blade shield;

2. In the above described technical solution, in order to make the blade holder and blade shield of the blade assembly smoothly transit from a locking state to a deadlocking state, the side of said locking block adjacent to the first front locking channel is an inclined surface and the side of locking block adjacent to the deadlock channel is a vertical surface.

3. In the above described technical solution, in order to make the blade assembly itself useful as a independent mini-scalpel or used as a handled scalpel after insertion of the handle, the said blade holder is provided with a second flexible cantilever. One side of the second flexible cantilever is provided with a first locking protrusion, lateral unlocking button and first inclined block; the side of the blade shield is provided with a second sliding channel for said lateral unlocking button, so that the lateral unlocking button is located in the second sliding channel. The second sliding channel is provided with a front indent at the front end and provided with a rear indent at the rear end. The said first locking protrusion mates with the front indent to lock the blade in an open state with respect to the blade shield and the first locking protrusion mates with the rear indent to lock the blade in a closed state with respect to the blade shield. Pressing the lateral unlocking button could release the mating state of the first locking protrusion and front indent or the mating state of the first locking protrusion and rear indent; the said first inclined block is used to mate with the third locking protrusion set at the front end of the handle. When the handle is connected with the blade holder, the third locking protrusion acts on the first inclined block to force the second flexible cantilever to be flexed, so that the first locking protrusion leaves its original position to be unable to engage the front indent or rear indent; when the handle is pulled out, the third locking protrusion is separated from the first inclined block, the second flexible cantilever automatically returns to its initial position resiliently and brings the first locking protrusion to return to its initial position, so that the first locking protrusion could engage the front indent or rear indent.

In order to achieve the above object, the present invention provides the technical solution of a reusable scalpel handle: a kind of reusable handle, wherein: the said handle is provided with a second inclined block used to engage the locking block on the flexible arm at the rear end of the blade holder. When the handle is inserted into the blade assembly to be connected with the blade holder, the second inclined block acts on the locking block to force the flexible arm to be flexed and force the protrusion block of the flexible arm to extend into the clearance opening in the inner wall of the blade shield with a sideward movement. After the second inclined block travels across the locking block, the flexible arm automatically returns to its initial position resiliently and the second inclined block engages the locking block to connect the handle and blade holder; during removal of the handle, the second inclined block draws the blade holder backward with respect to the blade shield through the locking block to force the protrusion block to misalign with the clearance opening. In this condition, the handle cannot be re-inserted into the blade assembly to be connected with the blade holder as the protrusion block cannot make side movement through the clearance opening.

The above described technical solution is explained as follows:

1. In the above described technical solution, in order to provide better mating of the handle and blade holder, the said handle is provided with a third locking protrusion at its front end used to mate with the first inclined block on the second flexible cantilever of the blade holder. When the handle is connected with the blade holder, the third locking protrusion acts on the first inclined block to force the second flexible cantilever to be flexed, so that the first locking protrusion on the second flexible cantilever leaves its original position to be unable to engage the front indent or rear indent of the blade shield; when the handle is pulled out, the third locking protrusion is separated from the first inclined block, the second flexible cantilever automatically returns to its initial position resiliently and brings the first locking protrusion to return to its initial position, so that the first locking protrusion could engage the front indent or rear indent.

2. In the above described technical solution, in order to effectively control the opening and closing operation of the blade with respect to the blade shield and the locking in the opening or closing state after the handle is inserted into the blade holder, the said handle is provided with a third sliding channel used to connect the first sliding channel of the blade holder. When the handle and blade holder are connected, the third sliding channel and first sliding channel are abutted, so that the first protrusion of the blade shield could slide along the first sliding channel to the third sliding channel. The said third sliding channel is provided with a first rear locking channel at the rear end and the first rear locking channel is connected with the rear end of the third sliding channel. When the first protrusion is located in the first rear locking channel, the blade extends out of the blade shield and the blade holder and blade are in a locking state with respect to the blade shield.

Furthermore: the said third sliding channel and first rear locking channel are set on one lateral face of the handle, and the fourth sliding channel is set on the opposite lateral face of handle at the corresponding position to the first sliding channel and third sliding channel. The fourth sliding channel is provided with a second front locking channel at its front end, which is connected with the front end of the fourth sliding channel and the fourth sliding channel is provided with a second rear locking channel at its rear end, which is connected with the rear end of the fourth sliding channel. The positions of the second front locking channel and first front locking channel are corresponding and the positions of the second rear locking channel and first rear locking channel are corresponding; the said fourth sliding channel, second front locking channel and second rear locking channel are used to work with the second protrusion of the second locking protrusion on the blade shield.

3. In the above described technical solution, in order to ensure more reliable connection of the handle and blade holder, the said handle is provided with a lower indent used to work with the protrusion of the blade holder. When the handle and blade holder are connected, the said lower indent engages the upper protrusion.

4. In the above described technical solution, the said handle is a reusable component and it could be made of metal material or nonmetal material. A handle made of metal material is more popular with doctors, as it's heavier and it has high strength and good "feel".

The particular design concept and operating principle of the present invention is: the scalpel of the present invention consists of a disposable blade assembly and reusable handle, wherein:

1. The blade holder of the present invention is provided with a flexible arm at the rear end which extends backward. The flexible arm is provided with a protrusion block at the end of the flexible arm. The inner wall of the blade shield is provided with a clearance opening for said protrusion block. Under the initial locating condition, the protrusion block faces the clearance opening. When the handle is inserted into the blade assembly to be connected with the blade holder, the flexible arm is flexed and forces the protrusion block to extend into the clearance opening with a sideward movement, so that the blade and the blade holder are connected. During removal of the handle, the handle draws the blade holder backward with respect to the blade shield to force the protrusion block to misalign with the clearance opening. In this condition, the handle cannot be inserted into the blade assembly to be connected with the blade holder as the protrusion block cannot make sideward movement through the clearance opening. Thus, it eliminates the possibility of reusing the combination of the blade assembly and handle to achieve the safety objective of a single use blade assembly.

2. In the present invention, the deadlock channel is set in front of the first front locking channel and the locking block is set between the deadlock channel and first front locking channel. After the scalpel is used pushing or pulling the blade shield further forward makes the first protrusion travel from the first front locking channel across the locking block to fall into the deadlock channel, with the blade arranged inside the blade shield. The blade holder and blade are thus in a deadlocking state with respect to the blade shield, so that the blade cannot be reused; Additionally, after the scalpel is used, the removal of the handle will make the second inclined block on the handle draw the blade holder backward with respect to the blade shield through the locking block to force the first protrusion to travel across the locking block to fall in the deadlock channel and end a in deadlocking state, so that it cannot be reused. As the blade holder and blade of the blade assembly are thus permanently locked with respect to the blade shield in the deadlocking state, the safety problem of reusing scalpel is eliminated.

The number description of the above described drawings is as follows:
1. blade holder; 10. fifth sliding channel; 11. first front locking channel; 12. first sliding channel; 13. first locking protrusion; 14. lateral unlocking button; 140. second flexible cantilever; 15. first inclined block; 16. locking block; 17. flexible arm; 171. locking block; 172. protrusion block; 18. upper protrusion; 19. deadlock channel;
2. blade;
3. blade shield; 31. top unlocking button; 32. second locking protrusion; 321. first protrusion; 322. second protrusion; 33. second sliding channel; 34. front indent; 35. rear indent; 36. protruding rib; 37. clearance opening; 38. window;
4. handle; 41. third sliding channel; 42. first rear locking channel; 43. fourth sliding channel; 44. second inclined block; 45. lower indent; 46. third locking protrusion; 47. second front locking channel; 48. second rear locking channel; 49. sixth sliding channel.

SPECIFIC EMBODIMENT

With reference to the accompanying drawings and embodiment, the present invention will be described in detail.

According to the detailed description of an embodiment of present invention, the relevant content of the present invention is explained as follows:

1. In the present invention, the "front" in said "front portion" and "front end" means the direction in which the blade tip points with respect to the scalpel. The "rear" in said "rear portion" and "rear end" means the direction opposite to the "front".

2. In the present invention, the said "locking state" means the temporary locking state of the blade holder and blade with respect to the blade shield. The locking state can be released by pressing the top unlocking button. The said "deadlocking state" is different from the locking state in that the deadlocking state means a state of permanently locking the blade holder and blade with respect to the blade shield. The deadlocking state is a permanent condition and can only be released by willful damage or misuse.

3. In the present invention, the said "initial locating state" means the final assembly state during fabrication of the blade assembly.

4. The present invention relates to the disposable blade assembly and reusable handle to complete a scalpel provided as a complete set or individually packed and sold. Therefore, the disposable blade assembly and reusable handle of this embodiment will be described from a complete scalpel perspective, so that those skilled in the art could have better and more accurate understanding and knowledge of present invention.

Embodiment

A Kind of Safe Shielded and Handled Scalpel

Figure 1:
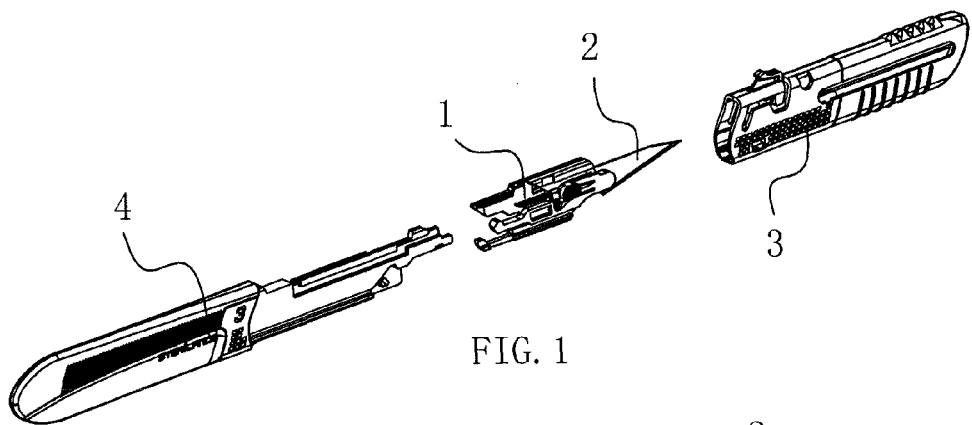
FIG. 1 is the exploded perspective view of a scalpel of the present invention.

Refer to FIG. 1. The scalpel consists of a disposable blade assembly and reusable handle, wherein the said blade assembly consists of a blade 2, blade holder 1 and blade shield 3. The blade 2 is fixed in a front portion of blade holder 1 and blade shield 3 is slidably mounted onto blade holder 1. Reusable means it could be used repeatedly.

The following is a detailed description of blade shield 3, blade holder 1 and handle 4.

Refer to FIGS. 2 to 11. The blade assembly consists of blade 2 (see FIG. 2), blade holder 1 (see FIGS. 2 and 4) and blade shield 3 (see FIGS. 5 and 6). The blade 2 is fixed in the front portion of blade holder 1 and blade shield 3 is slidably mounted onto blade holder 1.

Figure 4:
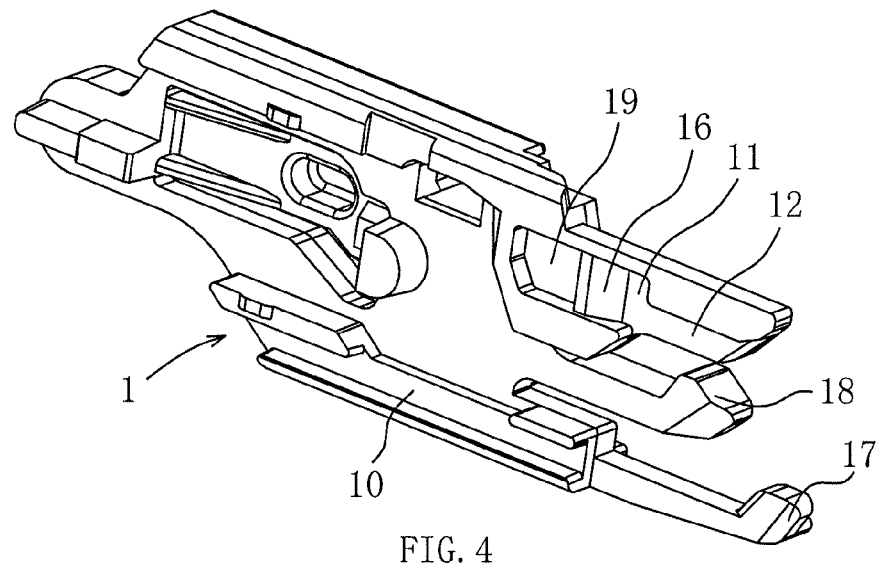
FIG. 4 is the back view illustrating the blade holder of the present invention.
Figure 5:
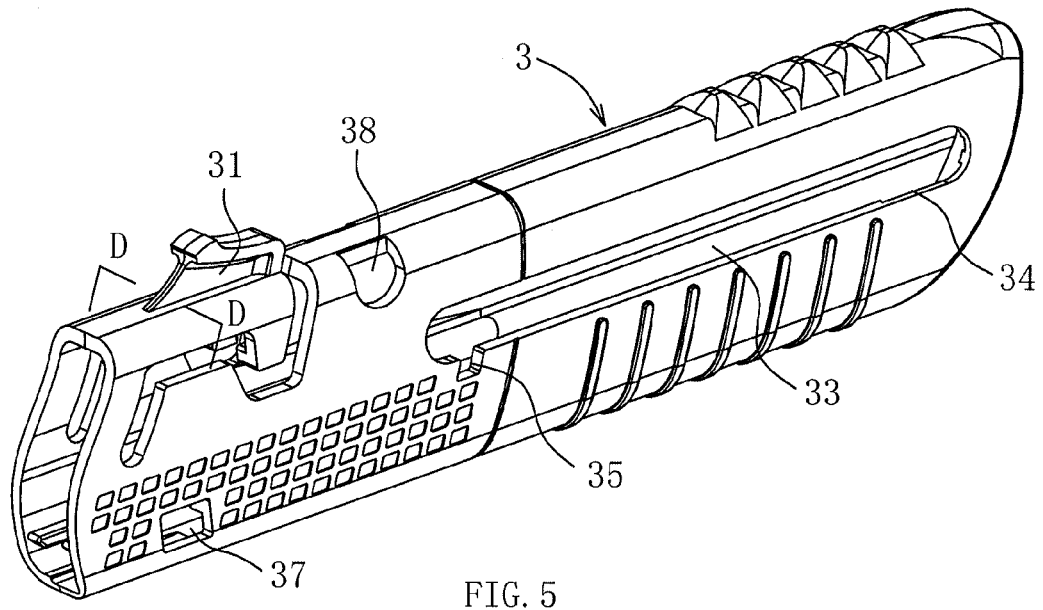
FIG. 5 is the front view illustrating the blade shield of the present invention.
Figure 6:
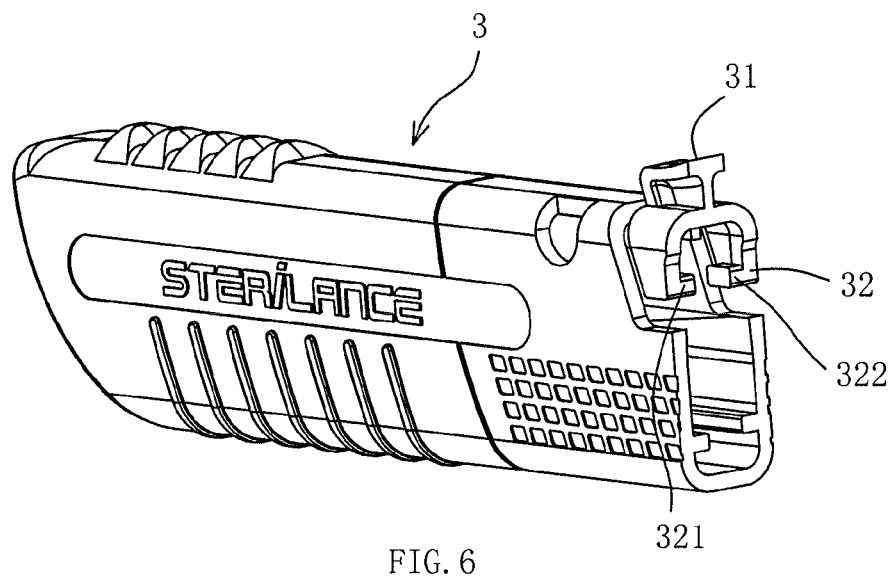
FIG. 6 is the section view along line D-D of FIG. 5.
Figure 7:
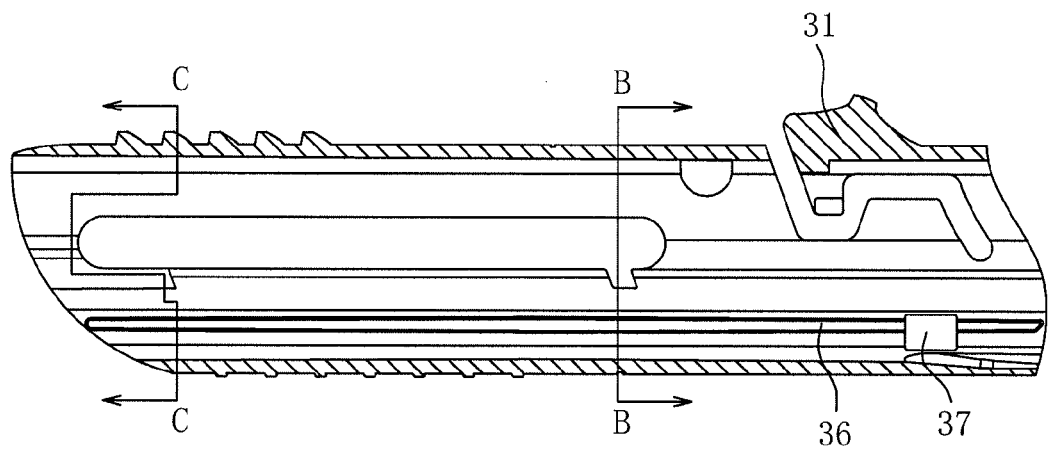
FIG. 7 is the main section view of FIG. 5.
Figures 8, 9:
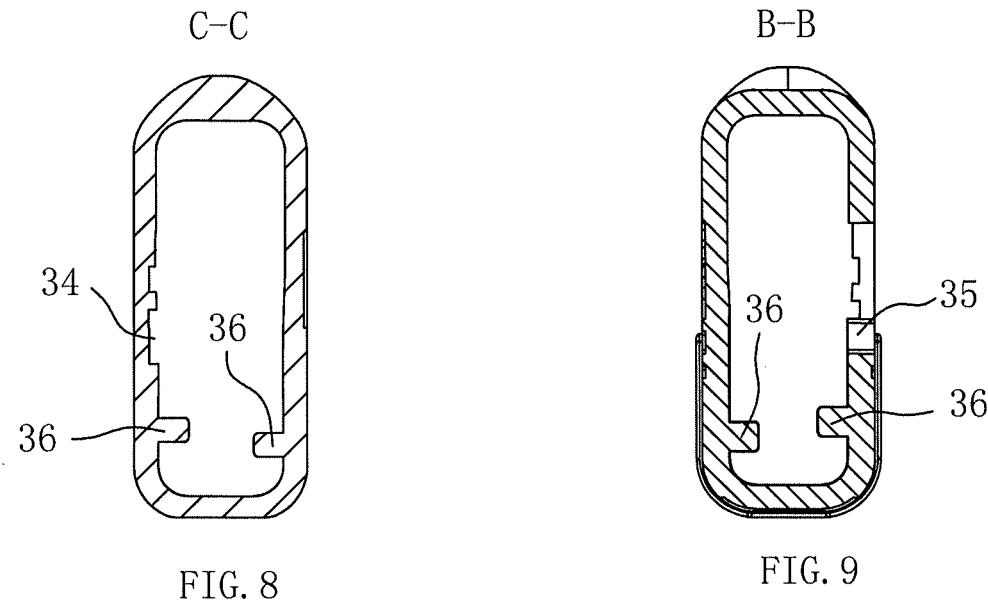
FIG. 8 is the section view along line C-C of FIG. 7.
FIG. 9 is the section view along line B-B of FIG. 7.

The said blade shield 3 is provided with one top unlocking button 31 and top unlocking button 31 is the first flexible cantilever structure on the blade shield 3 (see FIGS. 5 and 7). The first flexible cantilever is provided with second locking protrusion 32 (see FIG. 6) and second locking protrusion 32 includes a first protrusion 321. The blade holder 1 is provided with first sliding channel 12 for first protrusion 321 correspondingly (see FIG. 4), and the first sliding channel 12 is arranged along the blade holder 1 with respect to the sliding direction of blade shield 3. The first sliding channel 12 is provided with first front locking channel 11 at its front end and first front locking channel 11 is connected with the front end of first sliding channel 12. The deadlock channel 19 is set in front of first front locking channel 11 (see FIG. 4) and locking block 16 is set between deadlock channel 19 and first front locking channel 11. During the operation process of the scalpel, the first protrusion 321 enables the following different states when it mates with first front locking channel 11, first sliding channel 12 and deadlock channel 19 respectively:

a. When first protrusion 321 is located in first front locking channel 11, the blade 2 is arranged inside blade shield 3 and the blade holder 1 and blade 2 are in a locking state with respect to blade shield 3 and the blade holder 1 and blade 2 are temporarily locked with respect to blade shield 3 in the locking state;

b. When top unlocking button 31 is pressed, top unlocking button 31 forces first protrusion 321 to move from first front locking channel 11 to first sliding channel 12 and in such state, the blade shield 3 is allowed to move with respect to blade holder 1 and blade 2;

c. When first protrusion 321 travels from first front locking channel 11 across the locking block 16 to fall in the deadlock channel 19, the blade 2 is arranged inside blade shield 3 and the blade holder 1 and blade 2 are in a deadlocking state with respect to blade shield 3 and the deadlocking state could only be released by damage.

Figure 2:
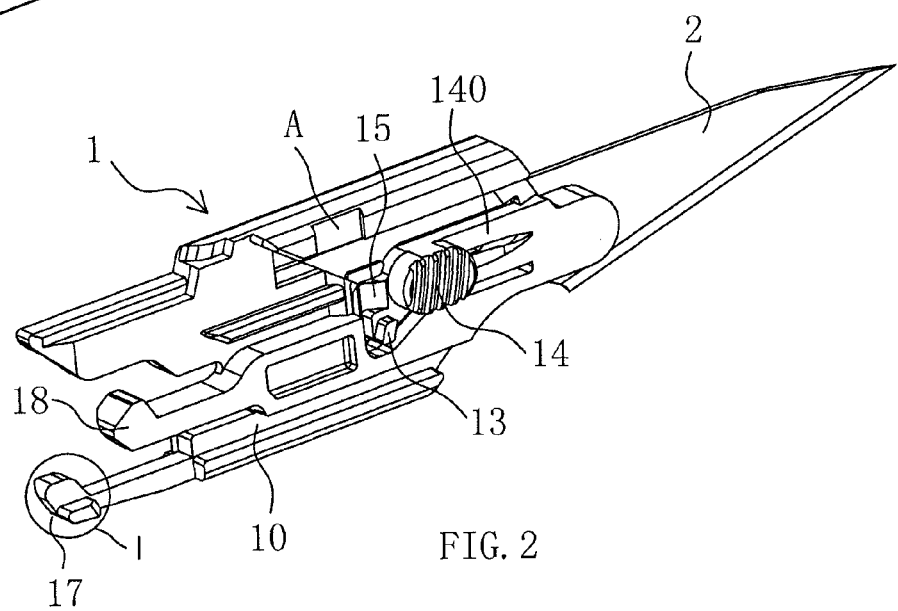
FIG. 2 is the front view illustrating the blade holder and blade of the present invention.
Figure 3:
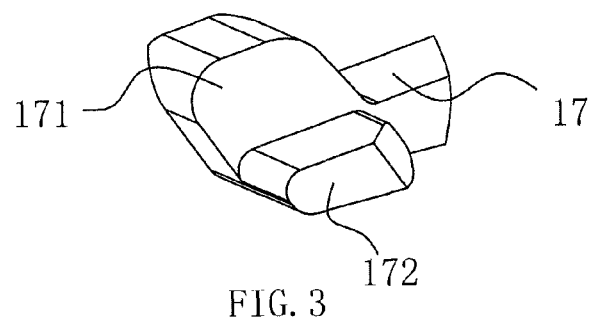
FIG. 3 is the enlarged view of structure I in FIG. 1.

The said blade holder 1 is provided with a flexible arm 17 at the rear end which extends backward (see FIG. 2) and the flexible arm 17 is provided with a locking block 171 and a protrusion block 172 (see FIG. 3). The protrusion block 172 extends toward the inner wall of blade shield 3 in the assembly state. The inner wall of blade shield 3 is provided with a clearance opening 37 for said protrusion block 172 (see FIG. 5) and the handle 4 is provided with second inclined block 44 at its front end for said corresponding locking block 171 (see FIG. 10). In the initial locating state (the final assembly state of the blade assembly), the first protrusion 321 of said blade assembly is located inside first front locking channel 11 and the protrusion block 172 faces the clearance opening 37. When the handle 4 is inserted into the blade assembly to be connected with blade holder 1, the second inclined block 44 acts on locking block 171 to force the flexible arm 17 to be flexed and force the protrusion block 172 to extend into clearance opening 37 with sideward movement. After the second inclined block 44 travels across the locking block 171, the flexible arm 17 automatically returns to its initial position resiliently and the second inclined block 44 engages the locking block 171 to connect the handle 4 and blade holder 1; During removal of the handle, the second inclined block 44 draws blade holder 1 backward with respect to blade shield 3 through locking block 171 to force the first protrusion 321 to travel across locking block 16 to fall in deadlock channel 19 to enter a deadlocking state and force the protrusion block 172 to misalign the clearance opening 37. In such state, the handle 4 cannot be re-inserted into the blade assembly to be connected with blade holder 1 as the protrusion block 172 could not make sideward movement through clearance opening 37.

In order to make blade holder 1 and blade shield 3 of blade assembly smoothly transit from a locking state to a deadlocking state, the side of said locking block 16 adjacent to first front locking channel 11 is an inclined surface and the side of locking block 16 adjacent to deadlock channel 19 is a vertical surface (see FIG. 4).

In order to use the blade assembly as a handled scalpel after connection of the blade assembly and handle 4, the said blade holder 1 is provided with second flexible cantilever 140 (see FIG. 2). The second flexible cantilever 140 is provided with first locking protrusion 13, lateral unlocking button 14 and first inclined block 15 on its one side. The blade shield 3 is provided with second sliding channel 33 for said lateral unlocking button 14 (see FIG. 5) on its side, so that lateral unlocking button 14 is located in second sliding channel 33. The second sliding channel 33 is provided with front indent 34 at its front end and provided with rear indent 35 at its rear end. The said front indent 34 is a shallow channel recessed into one lateral inner wall of blade shield 3 (see FIG. 8) and the said rear indent 35 is a concave hole connecting the inner wall and outer wall of blade shield 3 (see FIG. 9). The said first locking protrusion 13 mates with front indent 34 to lock the blade 2 in an open state with respect to blade shield 3 and first locking protrusion 13 mates with rear indent 35 to lock the blade 2 in a closed state with respect to blade shield 3. Pressing lateral unlocking button 14 can release the mating state of first locking protrusion 13 and front indent 34 or mating state of first locking protrusion 13 and rear indent 35.

Figure 10:
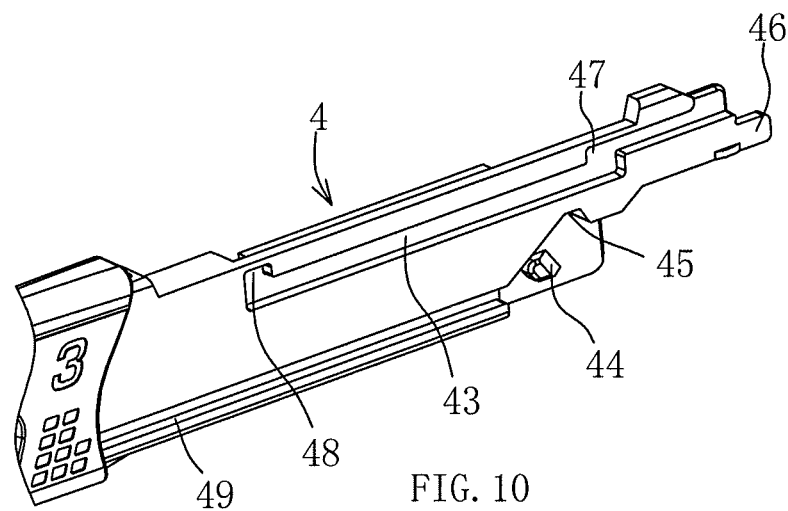
FIG. 10 is the front view illustrating the front end of the handle of the present invention.
Figure 11:
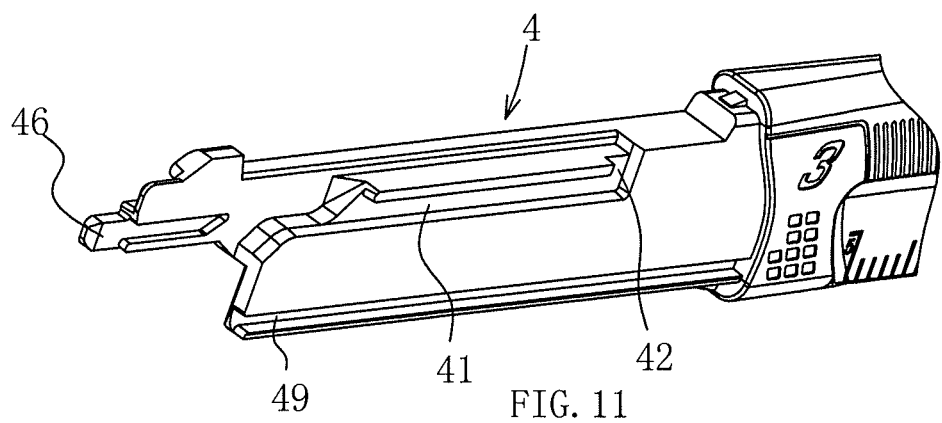
FIG. 11 is the back view illustrating the front end of the handle of the present invention.

The said first inclined block 15 (see FIG. 2) on the blade holder 1 is used to mate with third locking protrusion 46 (see. FIG. 10) set at front end of handle 4. When handle 4 is connected with blade holder 1, the third locking protrusion 46 acts on first inclined block 15 to force second flexible cantilever 140 to be flexed, so that first locking protrusion 13 leaves its original position to be unable to engage front indent 34 or rear indent 35. When the handle 4 is pulled out, the third locking protrusion 46 is separated from first inclined block 15, second flexible cantilever 140 automatically returns to initial position resiliently and brings the first locking protrusion 13 back to its initial position, so that first locking protrusion 13 can engage front indent 34 or rear indent 35.

In order to effectively control the opening and closing operation of blade 2 with respect to blade shield 3 and the locking in an opening or closing state after the blade assembly is inserted into handle 4, the said handle 4 is provided with the third sliding channel 41 (see FIG. 11) used to connect with the first sliding channel 12 of blade holder 1 (see FIG. 4). When the handle 4 and blade holder 1 are connected, the third sliding channel 41 and first sliding channel 12 are abutted, so that the first protrusion 321 of blade shield 3 can slide along first sliding channel 12 into third sliding channel 41. The said third sliding channel 41 is provided with first rear locking channel 42 at its rear end (see FIG. 11) and the first rear locking channel 42 is connected with the rear end of third sliding channel 41. When first protrusion 321 is located in first rear locking channel 42, the blade 2 extends out of blade shield 3 and blade holder 1 and blade 2 are in locking state with respect to blade shield 3.

The said first sliding channel 12 and first front locking channel 11 are set on one lateral face of blade holder 1, the said third sliding channel 41 and first rear locking channel 42 are set on one lateral face of handle 4, and fourth sliding channel 43 is set on the opposite lateral face of handle 4 at the corresponding position to first sliding channel 12 and third sliding channel 41 (see FIG. 10). The fourth sliding channel 43 is provided with second front locking channel 47 at its front end, which is connected with the front end of fourth sliding channel 43 and fourth sliding channel 43 is provided with second rear locking channel 48 at its rear end, which is connected with the rear end of fourth sliding channel 43. The positions of second front locking channel 47 and first front locking channel 11 are corresponding and the positions of second rear locking channel 48 and first rear locking channel 42 are corresponding. The second locking protrusion 32 includes second protrusion 322 (see FIG. 6), which is works with the fourth sliding channel 43, second front locking channel 47 and second rear locking channel 48.

In order to ensure more reliable connection of blade holder 1 and handle 4, the blade holder 1 is provided with one upper protrusion 18 (see FIGS. 2 and 4) and the said handle 4 is provided with lower indent 45 used to work with said upper protrusion 18 (see FIG. 10). When the handle 4 and blade holder 1 are connected, the said lower indent 45 engages the upper protrusion 18.

In order to ensure the smooth sliding of blade holder 1 and handle 4 inside the blade shield 3, the blade shield 3 is provided with a protruding rib 36 along the blade holder 1 with respect to the sliding direction of blade shield 3 (see FIGS. 8 and 9), and blade holder 1 is provided with fifth sliding channel 10 for said protruding rib 36 (see FIGS. 2 and 5). The matching of fifth sliding channel 10 and protruding rib 36 provides for the sliding connection of blade holder 1 inside blade shield 3. The said handle 4 is provided with sixth sliding channel 49 for said protruding rib 36 (see FIGS. 10 and 11) and when the handle 4 is inserted into the blade assembly, the matching of sixth sliding channel 49 and protruding rib 36 provides for the sliding connection of handle 4 inside blade shield 3.

Figure 12:
FIG. 12 through 17 illustrate the operation process of the present scalpel.

The operation procedure of the embodiment is described as follows with accompanying drawings:

FIG. 12 shows the separation of handle 4 and blade assembly before use of scalpel. Wherein, the blade assembly consists of blade 2, blade holder 1 and blade shield 3. The blade 2 is fixed in front portion of blade holder 1 and blade shield 3 is slidably mounted onto blade holder 1 and blade 2. In such a state, the blade 2 is arranged in blade shield 3 and the matching of first locking protrusion 13 of blade holder 1 and rear indent 35 of blade shield 3 locks the blade 2 in closing state with respect to blade shield 3. Meanwhile, the first protrusion 321 of blade shield 3 is located in the first front locking channel 11 of blade holder 1, which also locks the blade holder 1 and blade 2 in a locking state with respect to blade shield 3 for increased safety. In such a state, the protrusion block 172 at the end of flexible arm 17 of blade holder 1 faces the clearance opening 37 of blade shield 3. The blade holder 1 is provided with an indent at position A (see FIG. 2) and the indent could be colored. And the indent at position A could be seen from window 38 of blade shield 3 in the initial locating state.

Figure 13:
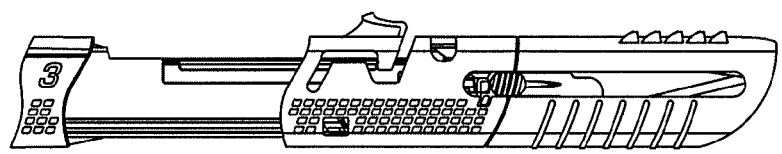

FIG. 13 shows the connection of scalpel handle 4 and blade assembly. When the front of handle 4 is inserted into the blade assembly to be connected with blade holder 1, the second inclined block 44 of handle 4 acts on locking block 171 at the end of flexible arm 17 of blade holder 1 to force the flexible arm 17 to be flexed and force the protrusion block 172 to extend into clearance opening 37 with sideward movement. After the second inclined block 44 travels across the locking block 171, the flexible arm 17 automatically returns to initial position resiliently and the second inclined block 44 engages the locking block 171 to connect the handle 4 and blade holder 1; When handle 4 and blade holder 1 are connected, the lower indent 45 of handle 4 travels across the upper protrusion 18 of blade holder 1 for engagement for more reliable connection of handle 4 and blade holder 1. After the handle 4 is connected with blade holder 1, the third locking protrusion 46 at the front end of handle 4 acts on first inclined block 15 on blade holder 1 to force second flexible cantilever 140 of blade holder 1 to be flexed, so that first locking protrusion 13 of blade holder 1 leaves its original position to be unable to engage rear indent 35. Now the locking of third locking protrusion 13 of blade holder 1 and rear indent 35 of blade shield 3 is released. After the handle 4 is connected with blade holder 1, the first sliding channel 12 at the back side of blade holder 1 and third sliding channel 41 at the back side of handle 4 are abutted and the second protrusion 322 of blade shield 3 is inserted into second front locking channel 47 on the front side of handle 4.

Figure 14:
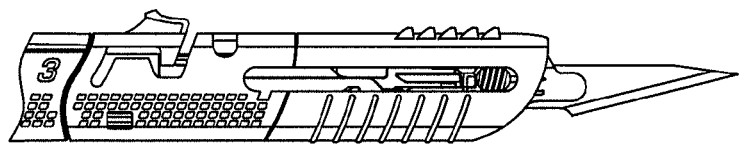

FIG. 14 shows the operation state after connection of scalpel handle 4 and blade assembly and opening of blade 2. The process of opening blade 2 is: in the state as shown in FIG. 13, when top unlocking button 31 is pressed, top unlocking button 31 forces first protrusion 321 to move from first front locking channel 11 at the back side of the scalpel to first sliding channel 12 and forces second protrusion 322 to move from second front locking channel 47 at the front side of the scalpel to fourth sliding channel 43. Then, the blade shield 3 may be moved backward and during movement, the first protrusion 321 at the back side moves along first sliding channel 12 to third sliding channel 41 and second protrusion 322 at the front side moves backwards along fourth sliding channel 43 until the first protrusion 321 at the back side falls into first rear locking channel 42 and the second protrusion 322 at the front side falls into second rear locking channel 48 to enter a locking state when the blade 2 is opened. Now, the scalpel can be used for surgery.

Figure 15:
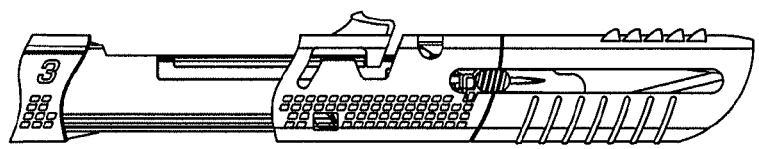

FIG. 15 shows the protection state of closing blade 2 after use of the scalpel. The process of closing blade 2 is: in the state as shown in FIG. 14, when top unlocking button 31 is pressed, top unlocking button 31 forces first protrusion 321 at the back side to move from first rear locking channel 42 to fall into third sliding channel 41 and forces second protrusion 322 at the front side to move from second rear locking channel 48 to fall into fourth sliding channel 43. Then, the blade shield 3 may move forward until the first protrusion 321 at the back side falls into first front locking channel 11 and the second protrusion 322 at the front side falls into second front locking channel 47 to enter a locking state when the blade 2 is closed.

Figure 16:
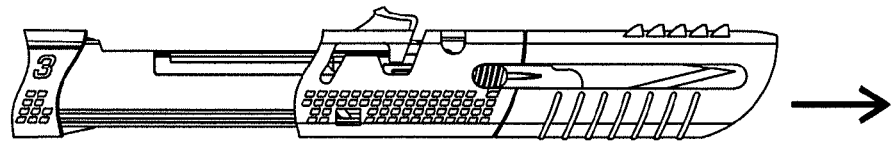

FIG. 16 shows the deadlocking state after use of the scalpel. The process is: in the state as shown in FIG. 15, continued movement of the blade shield 3 forward forces first protrusion 321 at the back side to travel from first front locking channel 11 over the inclined surface across locking block 16 to fall into deadlock channel 19. As the side of locking block 16 adjacent to deadlock channel 19 is a vertical surface, which forms the barrier, the first protrusion 321 cannot move backwards and it enters the permanent deadlocking state.

Figure 17:
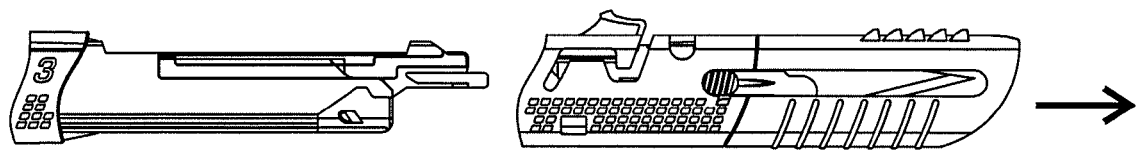

FIG. 17 shows the state of pulling handle 4 out of the blade assembly after use of the scalpel. The process is: in the state as shown in FIG. 16, to pull the handle 4 out of blade assembly is to separate the handle 4 and blade assembly. It shall be noted that: after removal of handle 4, the blade assembly is in a deadlocking state and cannot be reused. In such state, the protrusion block 172 misaligns with the clearance opening 37 and the handle 4 could not be re-inserted into the blade assembly to be connected with blade holder 1 as the protrusion block 172 cannot make a sideward movement through clearance opening 37. The blade assembly cannot be inserted into handle 4 for re-use after the use process above.

Additionally, if the process of entering the deadlocking state after use of the scalpel as shown in FIG. 16 is omitted i.e the blade shield 3 is not pushed forward to its extremity, it's possible to have the final effect as explained in FIG. 17 only by pulling out the handle 4. The reason is: during removal of handle 4, the second inclined block 44 draws blade holder 1 backward with respect to blade shield 3 through locking block 171 to force the first protrusion 321 to travel across locking block 16 to fall into deadlock channel 19 to enter a deadlocking state and force the protrusion block 172 to misalign with the clearance opening 37. In such state, the handle 4 cannot be re-inserted into the blade assembly to be connected with blade holder 1 as the protrusion block 172 cannot make sideward movement through clearance opening 37.

It should be noted that the above described embodiments are only for illustration of technical concept and characteristics of present invention with the purpose of making those skilled in the art understand the present invention, and thus these embodiments shall not limit the protection range of present invention. The equivalent changes or modifications according to spiritual essence of present invention shall fall in the protection scope of present invention.

The invention claimed is:

1. A disposable surgical blade assembly in which a handle can be inserted and removed but not re-inserted, the assembly comprising a blade, a blade holder and a blade shield, the blade being fixed in a front portion of the blade holder and the blade shield being slidably mounted on the blade holder, wherein:
   the blade holder is provided with a flexible arm at its rear end which extends backward and is used to connect the handle to the assembly, the flexible arm is provided with a locking block and a protrusion block, the locking block being used for engagement with a second inclined block at a front end of the handle and the protrusion block is used to prevent the deformation of the flexible arm, the protrusion block extending towards an inner wall of the blade shield and the inner wall of blade shield being provided with a clearance opening for said protrusion block, in an initial locating state of said blade assembly, the protrusion block faces the clearance opening;
   when the handle is inserted into the blade assembly to be connected with the blade holder, the second inclined block acts on the locking block to force the flexible arm to be flexed and force the protrusion block to extend into the clearance opening with sideward movement and after the second inclined block travels across the locking block, the flexible arm automatically returns to initial position resiliently and the second inclined block engages the locking block to connect the handle and blade holder;
   during removal of the handle, the second inclined block draws the blade holder backward with respect to the blade shield through the locking block to force the protrusion block to misalign with the clearance opening, whereby the handle cannot be re-inserted into the blade assembly to be connected with blade holder as the protrusion block cannot make sideward movement through the clearance opening.

2. The disposable surgical blade assembly of claim 1 wherein the blade shield is provided with a top unlocking button having a first flexible cantilever structure on the blade shield, the first flexible cantilever being provided with a second locking protrusion, which includes a first protrusion; the blade holder having a first sliding channel for the first protrusion, and the first sliding channel is arranged along the blade holder with respect to a sliding direction of the blade shield, the first sliding channel is provided with a first front locking channel at its front end, the first front locking channel being connected with the front end of the first sliding channel;
   wherein a deadlock channel is set in front of the first front locking channel and a locking block is set between the deadlock channel and the first front locking channel;
   wherein during an operation process with the handle inserted in the assembly for use as a scalpel, the first protrusion forms the following different states when it mates with the first front locking channel, the first sliding channel and the deadlock channel respectively:
   a. when the first protrusion is located in the first front locking channel, the blade is arranged inside the blade shield and the blade holder and the blade are in a locking state with respect to the blade shield;
   b. when the top unlocking button is pressed, the top unlocking button forces the first protrusion to move from the first front locking channel to the first sliding channel and in such a state, the blade shield is allowed to move with respect to the blade holder and the blade; and
   c. when the first protrusion travels from the first front locking channel across the locking block to fall into the deadlock channel, the blade is arranged inside the blade shield and the blade holder and the blade are in a deadlocking state with respect to the blade shield.

3. The disposable surgical blade assembly of claim 2 wherein a side of said locking block adjacent to the first front locking channel is an inclined surface and a side of the locking block adjacent to the deadlock channel is a vertical surface.

4. The disposable surgical blade assembly of claim 1, wherein the blade holder is provided with a second flexible cantilever, one side of the second flexible cantilever being provided with a first locking protrusion, a lateral unlocking button and a first inclined block; a side of the blade shield is provided with a second sliding channel for said lateral unlocking button, so that the lateral unlocking button is located in the second sliding channel, the second sliding channel being provided with a front indent at its front end and provided with a rear indent at its rear end, the first locking protrusion mating with the front indent to lock the blade in an open state with respect to the blade shield and the first locking protrusion mating with the rear indent to lock the blade in a closed state with respect to the blade shield, whereby pressing the lateral unlocking button can release the mating state of the first locking protrusion and the front indent or the mating state of the first locking protrusion and the rear indent; and
   wherein said first inclined block is used to mate with a third locking protrusion set at the front end of the handle, such that when the handle is connected with the blade holder, the third locking protrusion acts on the first inclined block to force the second flexible cantilever to be flexed, so that the first locking protrusion leaves its original position to be unable to engage the front indent or the rear indent; when the handle is pulled out, the third locking protrusion is separated from the first inclined block and the second flexible cantilever automatically returns to its initial position resiliently and brings the first locking protrusion back to its initial position, so that the first locking protrusion could engage front indent or rear indent.

5. A scalpel comprising the disposable surgical blade assembly according to claim 1 and a reusable handle wherein the handle comprises a second inclined block used to engage the locking block on the flexible arm at the rear end of the blade holder of the assembly,
   wherein when the handle is inserted into the blade assembly to be connected with the blade holder, the second inclined block acts on the locking block to force the flexible arm to be flexed and force the protrusion block of the flexible arm to extend into the clearance opening in the inner wall of the blade shield with sideward movement, and after the second inclined block travels across the locking block, the flexible arm automatically returns to its initial position resiliently and the second inclined block engages the locking block to connect the handle and blade holder; and wherein during removal of the handle from the blade assembly, the second inclined block draws the blade holder backward with respect to the blade shield through the locking block to force the protrusion block to misalign with the clearance opening, whereby in such a state, the handle cannot be inserted into the blade assembly to be connected with the blade holder as the protrusion block cannot make sideward movement through the clearance opening.

6. The scalpel claim 5 wherein the handle further comprises a third locking protrusion at its front end used to mate with a first inclined block on a second flexible cantilever of the blade holder, wherein:

when the handle is connected with the blade holder, the third locking protrusion acts on the first inclined block to force the second flexible cantilever to be flexed, so that a first locking protrusion on the second flexible cantilever leaves its original position to be unable to engage a front indent or a rear indent of the blade shield;

when the handle is pulled out, the third locking protrusion is separated from the first inclined block, the second flexible cantilever automatically returns to its initial position resiliently and brings the first locking protrusion back to its initial position, so that the first locking protrusion can engage the front indent or the rear indent.

7. The scalpel of claim 5 wherein the handle further comprises a third sliding channel used to connect with a first sliding channel of the blade holder;

wherein when the handle and the blade holder are connected, the third sliding channel and the first sliding channel are abutted, such that a first protrusion of the blade shield can slide along the first sliding channel to the third sliding channel;

wherein the third sliding channel is provided with a first rear locking channel at its rear end and the first rear locking channel is connected with the rear end of the third sliding channel; and wherein when a first protrusion is located in the first rear locking channel, the blade extends out of the blade shield and the blade holder and the blade are in a locking state with respect to the blade shield.

8. The scalpel of claim 7 wherein the third sliding channel and the first rear locking channel are set on one lateral face of the handle, and a fourth sliding channel is set on an opposite lateral face of the handle at the corresponding position to the first sliding channel and the third sliding channel;

wherein the fourth sliding channel is provided with a second front locking channel at its front end, which is connected with the front end of the fourth sliding channel and the fourth sliding channel is provided with a second rear locking channel at its rear end, the second rear locking channel being connected with the rear end of the fourth sliding channel;

wherein the positions of the second front locking channel and a first front locking channel of the blade holder are corresponding and the positions of the second rear locking channel and the first rear locking channel are corresponding; and wherein the fourth sliding channel, the second front locking channel and the second rear locking channel are used to work with a second protrusion of a second locking protrusion on the blade shield.

9. The scalpel of claim 5 wherein the handle is provided with a lower indent used to work with a protrusion of the blade holder when the handle and the blade holder are connected, the lower indent engaging the upper protrusion.

* * * * *